US00PP28735P3

(12) United States Plant Patent
Verlinden

(10) Patent No.: US PP28,735 P3
(45) Date of Patent: Dec. 5, 2017

(54) ***VERBENA* PLANT NAMED 'VEAZ0029'**

(50) Latin Name: *Verbena hybrida*
Varietal Denomination: VEAZ0029

(71) Applicant: SYNGENTA PARTICIPATIONS AG, Basel (CH)

(72) Inventor: Kathryn Verlinden, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,758

(22) Filed: Oct. 8, 2015

(65) Prior Publication Data

US 2016/0242343 P1 Aug. 18, 2016

(30) Foreign Application Priority Data

Feb. 18, 2015 (CA) ..... PBR 15-8532

(51) Int. Cl.
*A01H 5/02* (2006.01)

(52) U.S. Cl.
USPC ..... Plt./308

(58) Field of Classification Search
USPC ..... Plt./308
See application file for complete search history.

(56) References Cited

PUBLICATIONS

UPOV-PLUTO Plant Variety Database; International Union for the Protection of New Varieties of Plants; Jan. 4, 2017; citation for 'VEAZ0029'.*

* cited by examiner

*Primary Examiner* — Susan McCormick Ewoldt
(74) *Attorney, Agent, or Firm* — Dale Skalla

(57) ABSTRACT

A new *Verbena* plant named 'VEAZ0029' particularly distinguished by its medium sized inflorescences, medium sized flowers that are real white, medium green, undivided leaves, and an upright plant habit.

1 Drawing Sheet

Latin name of the genus and species of the plant claimed: *Verbena hybrida.*

Varietal denomination: 'VEAZ0029'.

BACKGROUND OF THE NEW PLANT

The present invention comprises a new *Verbena*, botanically known as *Verbena hybrida*, and hereinafter referred to by the variety name 'VEAZ0029'.

'VEAZ0029' is a product of a planned breeding program. The new cultivar has medium sized inflorescences, medium sized flowers that are real white, medium green, undivided leaves, and an upright plant habit.

'VEAZ0029' originated from an open pollinated cross made in July 2010 in the field in Enkhuizen, The Netherlands.

The female parent was an unpatented proprietary plant designated 'N0563-5', having a purple with white eye flower color, small leaves, and an upright plant habit.

The resulting seed was sown in February 2011 in a greenhouse in Enkhuizen, The Netherlands. 'VEAZ0029' was selected as one flowering plant within the progeny of the stated cross in May 2011.

The first act of asexual reproduction of 'VEAZ0029' was accomplished when vegetative cuttings were propagated from the initial selection in June 2011 in a greenhouse in Enkhuizen, The Netherlands.

BRIEF SUMMARY OF INVENTION

Horticultural examination of plants grown from cuttings of the plant initiated in the fall of 2011, and continuing thereafter, has demonstrated that the combination of characteristics as herein disclosed for 'VEAZ0029' are firmly fixed and are retained through successive generations of asexual reproduction.

'VEAZ0029' has not been observed under all possible environmental conditions. The phenotype may vary significantly with variations in environment such as temperature, light intensity, and day length.

A Plant Breeder's Right for this cultivar was applied for in Canada on Feb. 18, 2015, No. 15-8532.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0029' with colors being as true as possible with an illustration of this type.

Figure 1:
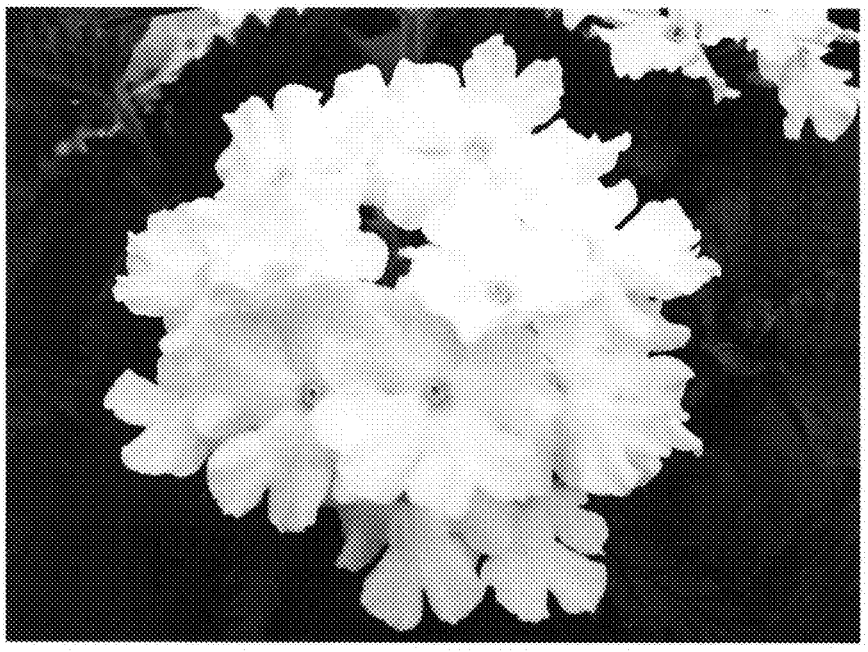
Figure 2:
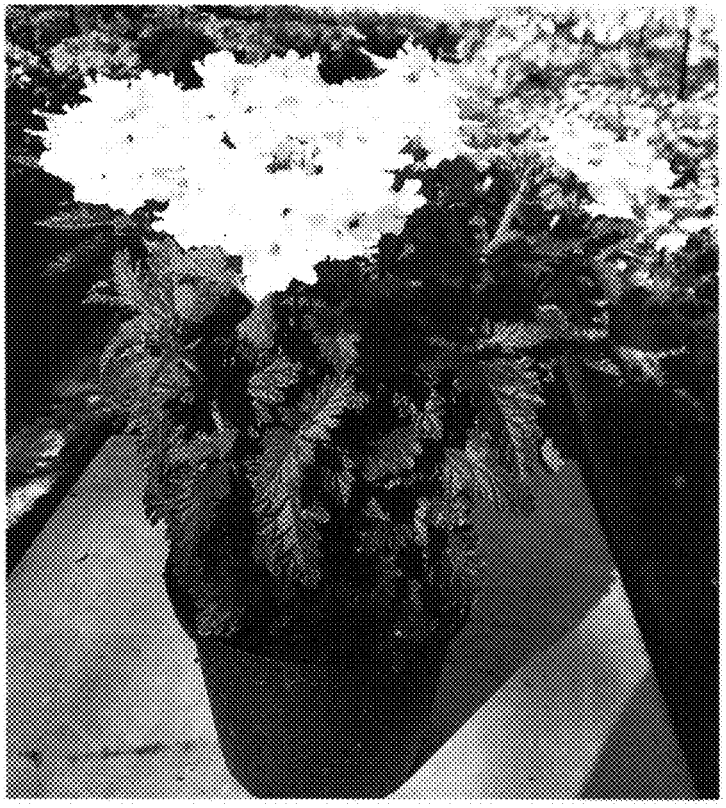

The photographic drawing in FIG. 1 shows a close view of an inflorescence of the new plant, and in FIG. 2 a whole flowering plant.

The aforementioned photographs were taken on Apr. 20, 2015 in Andijk, The Netherlands. The plants were about 10 weeks old and were grown in 12 cm pots.

DETAILED BOTANICAL DESCRIPTION

Color references are made to The Royal Horticultural Society Colour Chart (R.H.S.) 2001.

TABLE 1

DIFFERENCES BETWEEN THE NEW VARIETY 'VEAZ0029' AND A MOST SIMILAR VARIETY

| | 'VEAZ0029' | 'Sunvivaro', U.S. Plant Pat. No. 17,785 |
|---|---|---|
| Flower color: | Clear white | Yellowish White |
| Plant habit: | More upright | Mounding |
| Plant vigor: | More compact | More vigor |

Plant:

*Form, growth and habit.*—Herbaceous, initially upright, then outwardly spreading; vigorous and free-branching.
*Plant height.*—15.0 cm.
*Plant height (inflorescence included).*—18.0 cm.
*Plant width.*—33.0 cm.

Roots:
*Number of days to initiate and produce roots.*—10-14 days at about 22 degrees C.
*Type.*—Fine, fibrous, free branching.
*Color.*—RHS N155A but whiter.

Foliage:
*Arrangement.*—Opposite, simple.
*Immature, leaf color, upper surface.*—RHS 147B.
*Immature, leaf color, lower surface.*—RHS 137C.
*Mature, leaf color, upper surface.*—RHS 137B.
*Mature, leaf color, lower surface.*—RHS 136D.
*Length.*—About 4 cm.
*Width.*—3.0-3.2 cm.
*Shape.*—Ovate.
*Base shape.*—Cordate.
*Apex shape.*—Acute.
*Margin.*—Dentate.
*Texture, upper surface.*—Hirsute.
*Texture, lower surface.*—Hirsute.
*Color of veins, upper surface.*—RHS 144B.
*Color of veins, lower surface.*—RHS 144B.
*Pattern of veining.*—Pinnate.
*Petiole color.*—RHS 145C.
*Petiole length.*—1.1 cm.
*Petiole width.*—0.3 cm.
*Texture.*—Hirsute.

Stem:
*Branching characteristics.*—Most branches going upright.
*Quantity of main branches per plant.*—About 22.
*Color of stem.*—RHS 145B.
*Stem length.*—About 14-15 cm.
*Stem width.*—About 0.3 cm.
*Length of internodes.*—2.5-4 cm.
*Texture.*—Hirsute.
*Color of peduncle.*—RHS 138B.
*Length of peduncle.*—About 2-2.5 cm.
*Peduncle diameter.*—0.2 cm.
*Texture.*—Canescent.

Inflorescence:
*Type.*—Umbel-like, but actually a spike, umbrella shaped, large.
*Blooming habit.*—Flowers continuously through the summer months.
*Lastingness of individual blooms on the plant.*—About 4 days in the greenhouse.
*Fragrance.*—Slight jasmine fragrance.
*Number of inflorescences per plant.*—38 to 49 at various stages.
*Horizontal diameter of inflorescence.*—About 5.5 cm.
*Depth of inflorescence.*—3.0 cm.
*Number of florets per inflorescence (including any buds at the time).*—28-32.

Bud (just when opening/showing color):
*Color.*—RHS 155D.
*Length.*—0.45 cm.
*Width.*—0.45 cm.
*Shape.*—Tubular with a bulbous end.

Floret:
*Form.*—Sessile; salver-shape, composed of 5 partly fused petals with a base of a narrow tube.
*Immature color, upper surface.*—RHS 155D.
*Immature color, lower surface.*—RHS 155D.
*Mature color, upper surface.*—RHS 155D, but whiter.
*Mature color, lower surface.*—RHS 155D, but whiter.
*Floret diameter.*—2.3-2.7 cm.
*Floret length (depth).*—2.1-2.3 cm.
*Number of petals.*—Gamopetalous, 5 lobed.
*Petal length.*—1.0 cm.
*Petal width.*—1.0 cm.
*Shape.*—Obcordate.
*Apex shape.*—Emarginate.
*Margin.*—Entire.
*Petal texture, upper surface.*—Papillose; glabrous.
*Petal texture, lower surface.*—Papillose.
*Corolla tube length.*—1.5 cm.
*Corolla tube width.*—0.2 cm.
*Corolla tube color inside.*—RHS 155C.
*Tube color outside.*—RHS 155C near corolla to RHS 155D at base.
*Corolla texture, inside.*—Papillose.
*Corolla texture, outside.*—Glabrous.
*Throat hair color.*—RHS 155D but whiter.

Calyx:
*Type.*—Five sepals whose margins are fused to each other along their length, with a transparent membrane of less than 0.1 cm in width and with one smaller sepal attached to the base of the calyx.
*Color of sepals.*—RHS 143B.
*Length of sepals.*—1.0 cm.
*Width of sepals.*—0.2 cm.
*Sepal shape.*—Linear, but fused.
*Apex shape.*—Acute.
*Margins.*—Entire.
*Texture.*—Densely covered with short hair and many glandular hairs.

Reproductive organs:
*Gynoecium.*—
*Pistil.*—1.
*Pistil length.*—1.5 cm.
*Style color.*—RHS N144D.
*Style length.*—1.5 cm.
*Stigma color.*—RHS 144A.
*Ovary color.*—RHS 144B.
*Ovary length.*—0.25 cm.
*Ovary width.*—0.1 cm.
*Androecium.*—
*Stamens.*—Anthers and filaments fused to upper half of corolla tube; four anthers with two pollen sacs per anther.
*Color of filaments.*—RHS 151C.

*Filament length.*—0.25 cm.

*Anther color.*—RHS 151C.

*Anther length.*—0.15 cm.

*Pollen amount.*—None observed.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0029' substantially as illustrated and described herein.

* * * * *